US010117711B2

(12) United States Patent
Oberti

(10) Patent No.: US 10,117,711 B2
(45) Date of Patent: *Nov. 6, 2018

(54) APPARATUS AND METHOD FOR TREATING CARDIOVASCULAR DISEASES

(71) Applicant: THE CLEVELAND CLINIC FOUNDATION, Cleveland, OH (US)

(72) Inventor: Carlos M. Oberti, Chagrin Falls, OH (US)

(73) Assignee: THE CLEVELAND CLINIC FOUNDATION, Cleveland, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/231,928

(22) Filed: Aug. 9, 2016

(65) Prior Publication Data
US 2016/0346039 A1 Dec. 1, 2016

Related U.S. Application Data

(63) Continuation of application No. 14/202,790, filed on Mar. 10, 2014, now Pat. No. 9,480,552, and a
(Continued)

(51) Int. Cl.
*A61B 18/08* (2006.01)
*A61B 18/14* (2006.01)
(Continued)

(52) U.S. Cl.
CPC ............ *A61B 18/1492* (2013.01); *A61F 2/07* (2013.01); *A61B 18/08* (2013.01); *A61B 18/1815* (2013.01);
(Continued)

(58) Field of Classification Search
CPC ........ A61F 2/06; A61F 2/07; A61F 2002/072; A61F 2002/075; A61F 2002/821; A61B 18/08; A61B 18/14; A61B 18/1492
See application file for complete search history.

(56) References Cited

U.S. PATENT DOCUMENTS

| 5,935,162 | A | | 8/1999 | Dang | |
|---|---|---|---|---|---|
| 6,012,457 | A | * | 1/2000 | Lesh | ...................... A61B 18/10 128/898 |

(Continued)

FOREIGN PATENT DOCUMENTS

EP 1332724 A1 1/2003

*Primary Examiner* — Seema Mathew
(74) *Attorney, Agent, or Firm* — Tarolli, Sundheim, Covell & Tummino LLP

(57) ABSTRACT

A removable apparatus is provided for temporary implantation in a pulmonary vein for ablating atrial tissue surrounding the antrum of the pulmonary vein to treat atrial fibrillation in a subject. The apparatus comprises an electrically-insulated expandable support member and a retrieval mechanism. The support member has oppositely disposed proximal and distal end portions and a main body portion extending between the end portions. The proximal end portion includes at least one annularly disposed wing member, and has a free end defined by oppositely disposed first and second major surfaces. The at least one wing member includes at least one ablation element located at the free end thereof. The retrieval mechanism is for removing the support member and for energizing the at least one ablation element. The retrieval mechanism includes at least one electrically-conductive wire, which is separately connected to the at least one wing member.

16 Claims, 14 Drawing Sheets

Related U.S. Application Data continuation-in-part of application No. 12/357,520, filed on Jan. 22, 2009, now Pat. No. 8,652,201, which is a continuation-in-part of application No. 11/789,827, filed on Apr. 26, 2007, now Pat. No. 9,114,035.

(60) Provisional application No. 61/774,609, filed on Mar. 8, 2013, provisional application No. 60/795,256, filed on Apr. 26, 2006.

(51) Int. Cl.
    *A61F 2/07*     (2013.01)
    *A61B 18/00*     (2006.01)
    *A61B 18/18*     (2006.01)

(52) U.S. Cl.
    CPC ........ *A61B 2018/0022* (2013.01); *A61B 2018/00267* (2013.01); *A61B 2018/00279* (2013.01); *A61B 2018/00351* (2013.01); *A61B 2018/00375* (2013.01); *A61B 2018/00577* (2013.01); *A61B 2018/00791* (2013.01); *A61B 2018/1467* (2013.01); *A61B 2018/1475* (2013.01); *A61F 2002/072* (2013.01); *A61F 2002/075* (2013.01)

(56) References Cited

U.S. PATENT DOCUMENTS

| | | | |
|---|---|---|---|
| 6,632,223 B1 | 10/2003 | Keane | |
| 6,685,739 B2 * | 2/2004 | DiMatteo | A61F 2/2412 623/1.24 |
| 6,873,886 B1 | 3/2005 | Mullen et al. | |
| 6,973,339 B2 | 12/2005 | Govari | |
| 7,209,783 B2 | 4/2007 | Fellows et al. | |
| 7,255,695 B2 | 8/2007 | Falwell et al. | |
| 7,306,594 B2 | 12/2007 | Collins et al. | |
| 7,340,307 B2 | 3/2008 | Maguire et al. | |
| 7,429,261 B2 | 9/2008 | Kunis et al. | |
| 7,914,576 B2 * | 3/2011 | Navia | A61F 2/2445 623/2.36 |
| 8,712,550 B2 * | 4/2014 | Grunewald | A61B 18/1492 600/381 |
| 8,934,988 B2 | 1/2015 | Persson | |
| 9,814,522 B2 * | 11/2017 | Drews | A61B 18/1492 |
| 2002/0026233 A1 | 2/2002 | Shaknovich | |
| 2002/0177765 A1 * | 11/2002 | Bowe | A61B 18/1492 600/374 |
| 2003/0060821 A1 | 3/2003 | Hall et al. | |
| 2003/0069606 A1 * | 4/2003 | Girouard | A61F 2/958 607/3 |
| 2003/0204183 A1 | 10/2003 | Natale | |
| 2004/0106952 A1 | 6/2004 | Lafontaine | |
| 2004/0116965 A1 * | 6/2004 | Falkenberg | A61F 2/06 607/5 |
| 2004/0215310 A1 * | 10/2004 | Amirana | A61B 18/14 623/1.11 |
| 2005/0131503 A1 * | 6/2005 | Solem | A61B 17/320016 607/96 |
| 2006/0116666 A1 | 6/2006 | Cornelius | |
| 2007/0016280 A1 * | 1/2007 | Yacoby | A61F 2/88 623/1.11 |
| 2007/0083194 A1 * | 4/2007 | Kunis | A61B 18/1492 606/41 |
| 2007/0156211 A1 | 7/2007 | Ferren | |
| 2007/0173918 A1 * | 7/2007 | Dreher | A61F 2/958 623/1.11 |
| 2007/0239272 A1 | 10/2007 | Navia et al. | |
| 2008/0262337 A1 | 10/2008 | Falwell et al. | |
| 2008/0281391 A1 | 11/2008 | MacAdam et al. | |
| 2009/0131930 A1 * | 5/2009 | Gelbart | A61B 18/1492 606/41 |
| 2009/0177262 A1 | 7/2009 | Oberti et al. | |
| 2010/0087913 A1 | 4/2010 | Rabkin | |
| 2012/0089224 A1 * | 4/2012 | Haug | A61F 2/2418 623/2.17 |
| 2013/0178910 A1 | 7/2013 | Azamian | |
| 2014/0031785 A1 | 1/2014 | Schwagten | |
| 2015/0119881 A1 * | 4/2015 | Bagley | A61B 18/1492 606/41 |
| 2015/0150621 A1 | 6/2015 | Schwagten | |
| 2016/0051822 A1 * | 2/2016 | Guez | A61N 1/36114 607/122 |
| 2017/0156791 A1 * | 6/2017 | Govari | A61B 5/6853 |
| 2017/0281193 A1 * | 10/2017 | Asirvatham | A61B 17/12122 |

* cited by examiner

APPARATUS AND METHOD FOR TREATING CARDIOVASCULAR DISEASES

RELATED APPLICATIONS

This application is a continuation of U.S. patent application Ser. No. 14/202,790, filed Mar. 10, 2014 (which claims the benefit of U.S. Provisional Patent Application Ser. No. 61/774,609, filed Mar. 8, 2013), which is a continuation-in-part of U.S. patent application Ser. No. 12/357,520 (now U.S. Pat. No. 8,652,201), filed Jan. 22, 2009, which is a continuation-in-part of U.S. patent application Ser. No. 11/789,827 (now U.S. Pat. No. 9,114,035), filed Apr. 26, 2007, which claims priority from U.S. Provisional Patent Application Ser. No. 60/795,256, filed on Apr. 26, 2006. The subject matter of the aforementioned applications is hereby incorporated herein by reference in their entirety for all purposes

TECHNICAL FIELD

The present disclosure relates to the treatment of cardiovascular diseases and, more particularly, to an apparatus and method for treating cardiac conditions, such as atrial fibrillation.

BACKGROUND

The heart is, in essence, a pump that is responsible for circulating blood throughout the body. In a normally functioning heart, such circulation is caused by the generation of electrical impulses that, for example, increase or decrease the heart rate and/or the force of contraction in response to the demands of the circulatory system. If the electrical signal becomes disturbed in some way, the efficient pumping action of the heart may deteriorate, or even stop altogether.

Disturbance in the regular rhythmic beating of the heart is a common disorder seen in heart disease. Irregular rhythms (arrhythmia) can be a minor annoyance, or may indicate a serious problem. For example, arrhythmias may indicate an underlying abnormality of the heart muscle, valves or arteries, and includes the situation where the heart is beating too slowly (bradycardia) and also where the heart is beating too rapidly (tachycardia).

One particular type of cardiac arrhythmia, known as atrial fibrillation (AF), is a common cardiac rhythm disorder which can affect the quality of a patient's life and may be associated with significant morbidity. Atrial fibrillation is characterized by a rapid disorganized rhythm of the upper chambers of the heart (the atria). Instead of a single wavefront of electrical activation during regular rhythm, AF consists of multiple coexistent wavefronts with random re-entry. The condition may happen by itself (lone AF), may be related with hypertension, valvular disease, or may arise following cardiac surgery.

The etiology of AF is varied and has been hypothesized in some cases to have a genetic component. While medication is effective to control AF in some patients, other primary treatment modalities, such as endocardial ablation or surgical intervention, are often necessary for effective treatment. Endovascular approaches, for example, may be used to create lesions using an ablation catheter to block intra-atrial conduction. Primary treatments are not always satisfactory, however, as arrhythmias often reoccur in patients (20-50%) and thus additional secondary treatments, such as additional ablation procedures may be necessary. Such ablation procedures present several drawbacks, such as long procedure times that result in prolonged exposure to radiation for both patient and clinician. Additionally, ablation procedures can present a significant risk in pulmonary vein stenosis resulting from ablation within the pulmonary vein. Another potentially severe consequence could be the occurrence of a left atrial-esophageal fistula, which is typically lethal.

SUMMARY

In one aspect of the present disclosure, a removable endovascular and endocardial apparatus is provided for temporary implantation in a pulmonary vein for ablating atrial tissue surrounding the antrum of the pulmonary vein to treat atrial fibrillation (AF) in a subject. The apparatus comprises an electrically-insulated expandable support member and a retrieval mechanism. The support member has oppositely disposed proximal and distal end portions and a main body portion extending between the end portions for positioning in the pulmonary vein. The proximal end portion includes at least one annularly disposed wing member that extends from the main body portion. The at least one wing member has a free end and is defined by oppositely disposed first and second major surfaces. The distal end portion is adapted for insertion into the pulmonary vein to accurately position the proximal end portion at the antrum. When temporarily implanted, the first major surface is for facing the interior of the atrial chamber and the second major surface has a shape configured to conform to the surface topography of the atrial tissue surrounding the pulmonary vein. The at least one wing member includes at least one ablation element for delivering electrical energy to the atrial tissue. The at least one ablation element is located at the free end of the at least one wing member. The retrieval mechanism is for removing the expandable support member and, optionally, for energizing the at least one ablation element. The retrieval mechanism includes at least one electrically-conductive wire, which is separately connected to the at least one wing member.

In another aspect of the present disclosure, a method is provided for treating AF in a subject. One step of the method includes providing a removable apparatus comprising an electrically-insulated expandable support member and a retrieval mechanism. The expandable support member has oppositely disposed proximal and distal end portions and a main body portion extending between the end portions. The proximal end portion includes at least one annularly disposed wing member that extends from the main body portion. Each of the at least one wing member has a free end and being defined by oppositely disposed first and second major surfaces. Each of the at least one wing member includes at least one ablation element located at the free end thereof. The retrieval mechanism includes at least one electrically-conductive wire, which is separately connected to the at least one wing member. The expandable support member is inserted into a pulmonary vein so that the distal end portion of the main body portion is disposed in the lumen of the pulmonary vein, which can stabilize the expandable support member by ensuring stable contact during an ablation procedure. The at least one wing member is then deployed so that the second surface of the at least one member extends substantially radial to the main body portion of the expandable support member and firmly engages the atrial tissue surrounding the antrum of the pulmonary vein. Next, electrical energy is delivered to the at least one ablation element to substantially ablate the atrial tissue. The retrieval mechanism is then operated to collapse the expandable support member. The expandable support member is finally withdrawn from the pulmonary vein.

BRIEF DESCRIPTION OF THE DRAWINGS

The foregoing and other features of the present disclosure will become apparent to those skilled in the art to which the present disclosure relates upon reading the following description with reference to the accompanying drawings, in which.

DETAILED DESCRIPTION

Figure 1A:
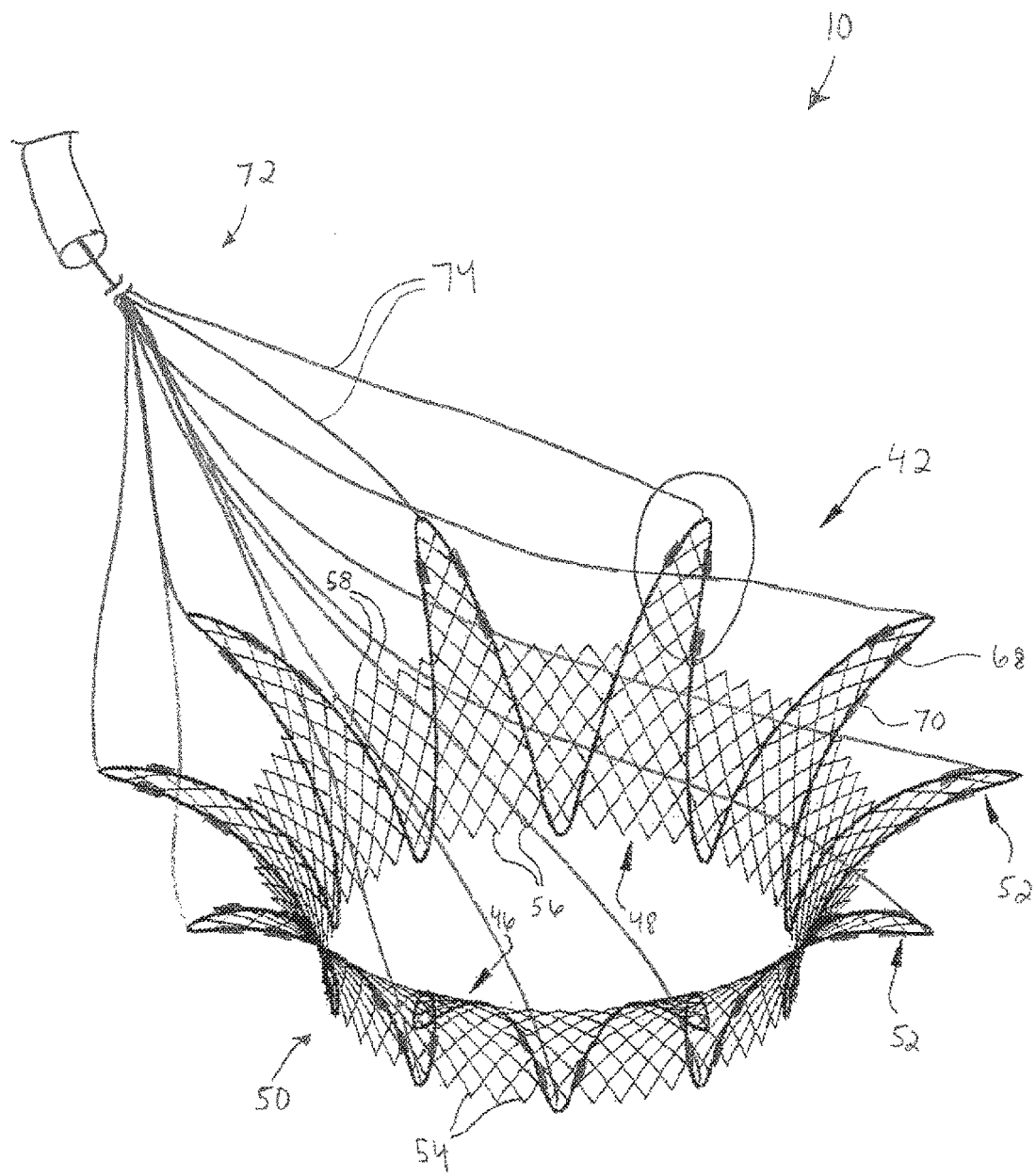
FIG. 1A is a perspective view showing an apparatus, in an expanded configuration, for temporary implantation in a pulmonary vein for ablating atrial tissue surrounding the antrum of the pulmonary vein to treat atrial fibrillation (AF) constructed in accordance with one aspect of the present disclosure.

Unless defined otherwise, all technical and scientific terms used herein have the same meaning as is commonly understood by one of skill in the art to which the present disclosure pertains.

In the context of the present disclosure, the terms "circumference" or "circumferential" can refer to a continuous path or line that forms an outer border or perimeter that surrounds and thereby defines an enclosed region of space. Such a continuous path can start at one location along the outer border or perimeter, and translates along the outer border or perimeter until it is completed at the original starting location to enclose the defined region of space. The related term "circumscribe" can mean to enclose, surround, or encompass a defined region of space. Therefore, a continuous line that is traced around a region of space and which starts and ends at the same location "circumscribes" the region of space and has a "circumference" defined by the distance the line travels as it translates along the path circumscribing the space. Still further, a circumferential path or element may include one or more of several shapes and may be, for example, circular, oblong, ovular, elliptical, or otherwise planar enclosures. A circumferential path may also be three-dimensional, such as two opposite-facing semi-circular paths in two different parallel or off-axis planes that are connected at their ends by line segments bridging between the planes.

As used herein, the term "circumferential conduction block" can refer to one or more lesions formed along a region of tissue (e.g., atrial tissue) that follows a circumferential path along the tissue adjacent an ostium of a pulmonary vein. In some instances, a circumferential conduction block can isolate electrical conduction between portions of the pulmonary vein wall and the surrounding atrial tissue.

As used herein, the terms "ablate" or "ablation" can refer to the substantial altering of the mechanical, electrical, chemical, or other structural nature of tissue (e.g., atrial tissue). In the context of intracardiac ablation applications, such as those described below, "ablation" can refer to sufficient altering of tissue properties to substantially block conduction of electrical signals from or through the ablated cardiac tissue.

As used herein, the term "ablation element" can refer to a variety of specific structures adapted to ablate a defined region of tissue (e.g., atrial tissue). In some instances, an ablation element can include an "energy emitting" element adapted to emit energy in an amount sufficient to ablate tissue when coupled to (and energized by) an energy source. In one example, and as described in more detail below, an ablation element can include: an electrode adapted for coupling to a direct current or alternating current source, such as a radiofrequency (RF) current source; an antenna element, which is energized by a microwave energy source; a heating element, such as a metallic element or other thermal conductor, which is energized to emit heat (e.g., by convective or conductive heat transfer) via resistive heating due to current flow or by optical heating with light; a light emitting element, such as a fiber optic element that transmits light sufficient to ablate tissue when coupled to a light source; or an ultrasonic element, such as an ultrasound crystal element adapted to emit ultrasonic sound waves sufficient to ablate tissue when coupled to a suitable excitation source.

As used herein, the term "subject" can be used interchangeably with the term "patient" and refer to any warm-blooded organism including, but not limited to, human beings, pigs, rats, mice, dogs, goats, sheep, horses, monkeys, apes, rabbits, cattle, etc.

Figure 1B:
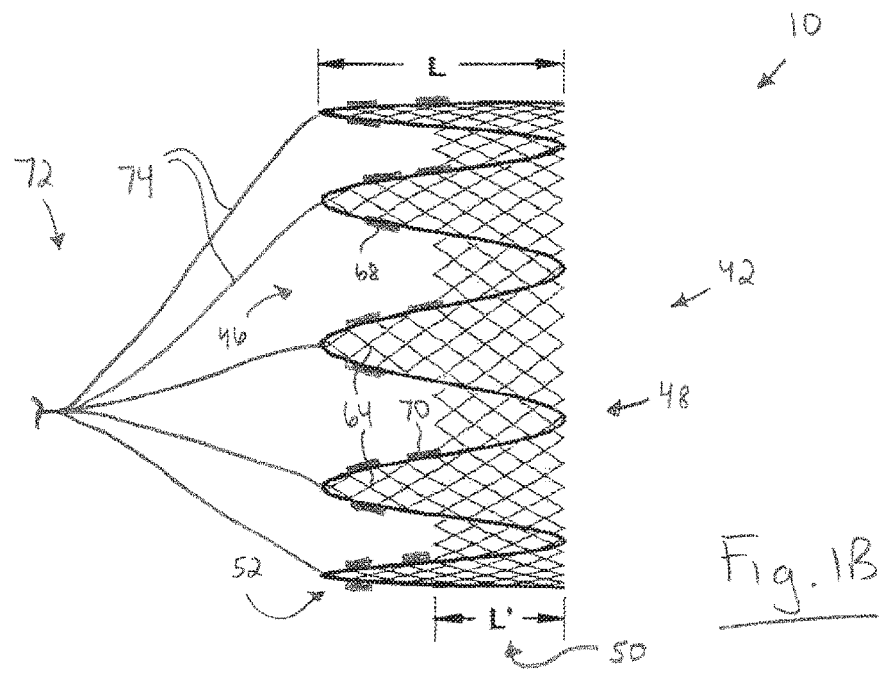
FIG. 1B is a cross-sectional view of the apparatus shown in FIG. 1A.
Figure 1C:
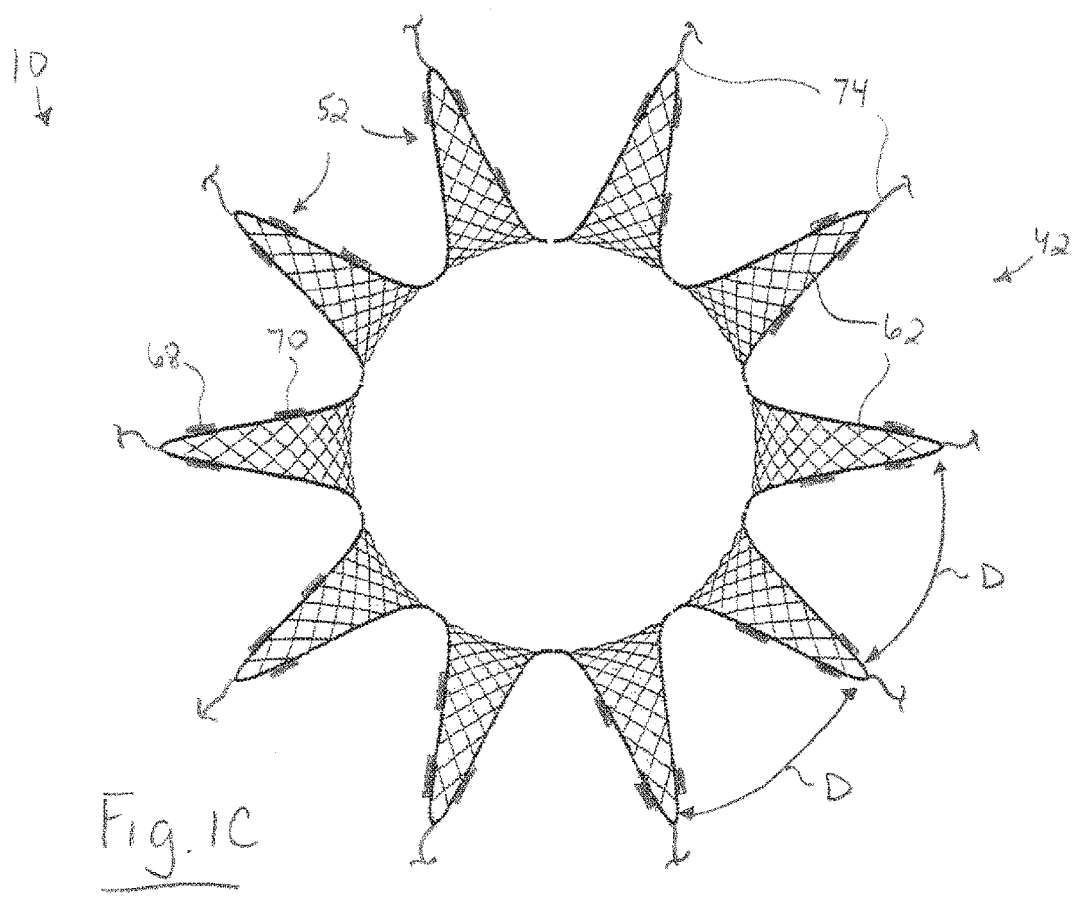
FIG. 1C is a top view of the apparatus shown in FIG. 1A.

The present disclosure relates to the treatment of cardiovascular diseases and, more particularly, to an apparatus and method for treating cardiac conditions, such as atrial fibrillation (AF). As representative of one aspect of the present disclosure, FIGS. 1A-C illustrate a removable apparatus 10 for treating cardiac arrhythmias, such as AF. Conventional AF ablation device and methods leave discontinuous lesions or, if enough time is allotted, a continuous lesion that takes an impractical amount of time to achieve. As described in more detail below, the present disclosure advantageously provides apparatus and methods that allow simultaneous and continuous lesion formation, which significantly improves effective conduction block and reduces the amount of time needed for the procedure. It will be understood that the apparatus 10 may be used to treat other cardiac arrhythmias including, but not limited to, premature atrial contraction, atrial flutter, supraventricular tachycardia, sick sinus syndrome, atrioventricular block, ventricular fibrillation, premature ventricular contraction, ventricular tachycardia, and other cardiovascular diseases such as heart failure, acute and chronic heart transplant rejection, and pulmonary arterial hypertension. Further, it is contemplated that the apparatus 10 may also be useful as a complimentary treatment to pacemaker implantation and/or defibrillator implantation.

While medication is effective to control AF in some patients, other primary treatment modalities, such as endocardial ablation or surgical intervention are often necessary for effective treatment. Results from catheter-based approaches to treat AF via RF ablation, for example, have improved significantly over the past decade. Current ablative AF treatments, however, require long procedure times and result in prolonged exposure to radiation for both the patient and clinician. Despite the advantages of current ablative AF treatments, recurrence of AF is frequent and therefore requires subsequent "re-do" procedures. Additionally, ablative RF treatments that target sites within the pulmonary vein carry a significant risk of pulmonary vein stenosis following such treatments.

Advantageously, the present disclosure provides an apparatus 10 and related methods for ablating atrial tissue surrounding the antrum of a pulmonary vein, without the associated risks noted above, to treat AF. As described in more detail below, the apparatus 10 is configured to provide controlled contact with atrial antrum tissue during an ablation procedure. Unlike conventional apparatus and methods for ablative RF treatments that target sites within the pulmonary vein, the present disclosure: (1) requires a lower amount of energy to be delivered to create a therapeutic lesion (e.g., by permitting simultaneous, continuous lesion formation); (2) reduces fluoroscopic radiation exposure for both the patient and the clinician; (3) protects endoluminal tissue of the pulmonary vein from ablation; (4) decreases the need for operator-dependent treatment administration, which improves delivery accuracy; and (5) significantly reduces procedure time. These advantages of the present disclosure, as well as others will be described below following a brief discussion of the relevant anatomy and physiology.

Figure 2:
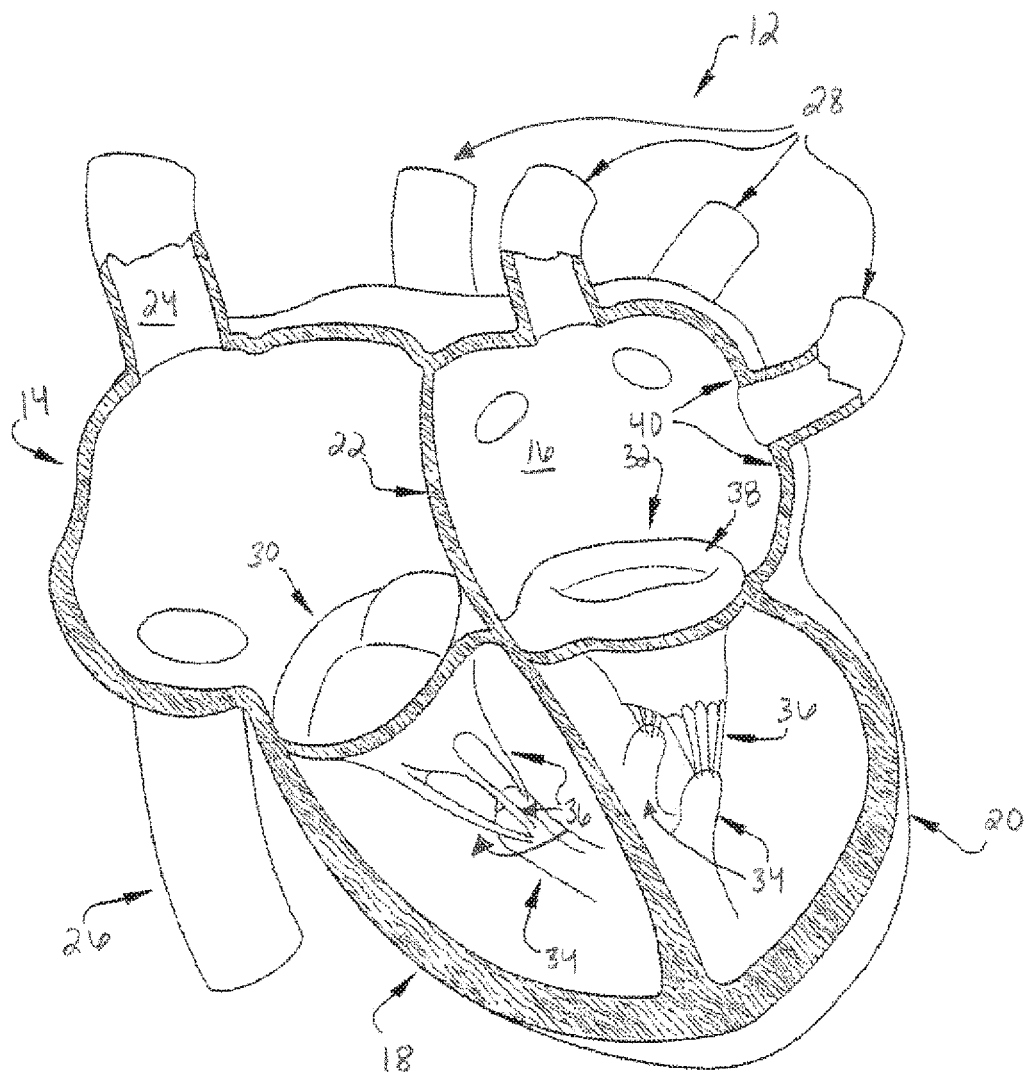
FIG. 2 is a cross-sectional schematic view of a human heart.

FIG. 2 schematically illustrates a human heart 12, which includes four chambers: the right and left atria 14 and 16; and the right and left ventricles 18 and 20. The right and left atria 14 and 16 are divided by the interatrial septum 22. The thin-walled right atrium 14 receives deoxygenated blood from the superior vena cava 24, the inferior vena cava 26, and the coronary sinuses (not shown). The thin-walled left atrium 16 receives oxygenated blood from pulmonary veins 28. The right and left ventricles 18 and 20 pump deoxygenated and oxygenated blood, respectively, from the right ventricle to the pulmonary circuit and from the left ventricle throughout the body, while the pocket-like semilunar pulmonary valve (not shown) and aortic valve (not shown) prevent reflux into the ventricles. Atrial blood is pumped through the atrioventricular orifices, guarded by the tri-leaflet tricuspid valve 30 on the right side of the heart 12 and the bi-leaflet mitral valve 32 on the left side of the heart, while ventricular blood is pumped through the pulmonary artery (not shown) and the aorta (not shown). The leaflets (not shown) of the mitral valve 32 are attached to the papillary muscles 34 in the left ventricle 20 by chordae tendineae 36. The leaflets of the mitral valve 32 extend across an annulus 38, which is an area of heart wall tissue at the junction of the atrial and ventricular walls that is relatively fibrous and significantly stronger than leaflet tissue. Similarly, the leaflets of the tricuspid valve 30 are attached to the papillary muscles 34 in the right ventricle 18 by chordae tendineae 36. The leaflets of the tricuspid valve 30 extend across an annulus (not shown in detail) at the junction of the atrial and ventricular walls.

Referring to FIGS. 1A-C, one aspect of the present invention includes a removable apparatus 10 for temporary implantation in a pulmonary vein 28. As described in more detail below, the apparatus 10 is configured for ablating atrial tissue surrounding the antrum 40 (FIG. 2) of a pulmonary vein 28. As shown in FIG. 1A, the apparatus 10 can include an electrically-insulated expandable support member 42 and a retrieval mechanism 72. The expandable support member 42 can include oppositely disposed proximal and distal end portions 46 and 48, and a main body portion 50 extending between the proximal and distal end portions. The proximal end portion 46 can include at least one annularly disposed wing member 52 that extends from the main body portion 50. In some instances, the main body portion 50 can have an annular or ring-like configuration adapted and shaped for implantation within the lumen of a pulmonary vein 28. For example, the distal end portion 48 of the expandable support member 42 can be configured for insertion into a pulmonary vein 28 to facilitate accurate positioning of the proximal end portion 46 about the antrum 40 of the pulmonary vein.

The expandable support member 42 is both flexible and resilient and, as discussed in more detail below, can be made of a shape memory material, such as Nitinol, stainless steel, or other suitable medical grade metal(s) or plastic(s) (e.g., poly(cyclohexane-1,4-diylacetone dimethylene ketal) and Polyzene-F) having shape memory characteristics. The expandable support member 42 may also be made of a radio-opaque material, or include radio-opaque markers to facilitate fluoroscopic visualization. The flexible and expandable properties of the expandable support member 42 facilitate percutaneous delivery of the apparatus 10, while also allowing at least a portion of the expandable support member to be secured within the lumen of a pulmonary vein 28.

Figure 3:
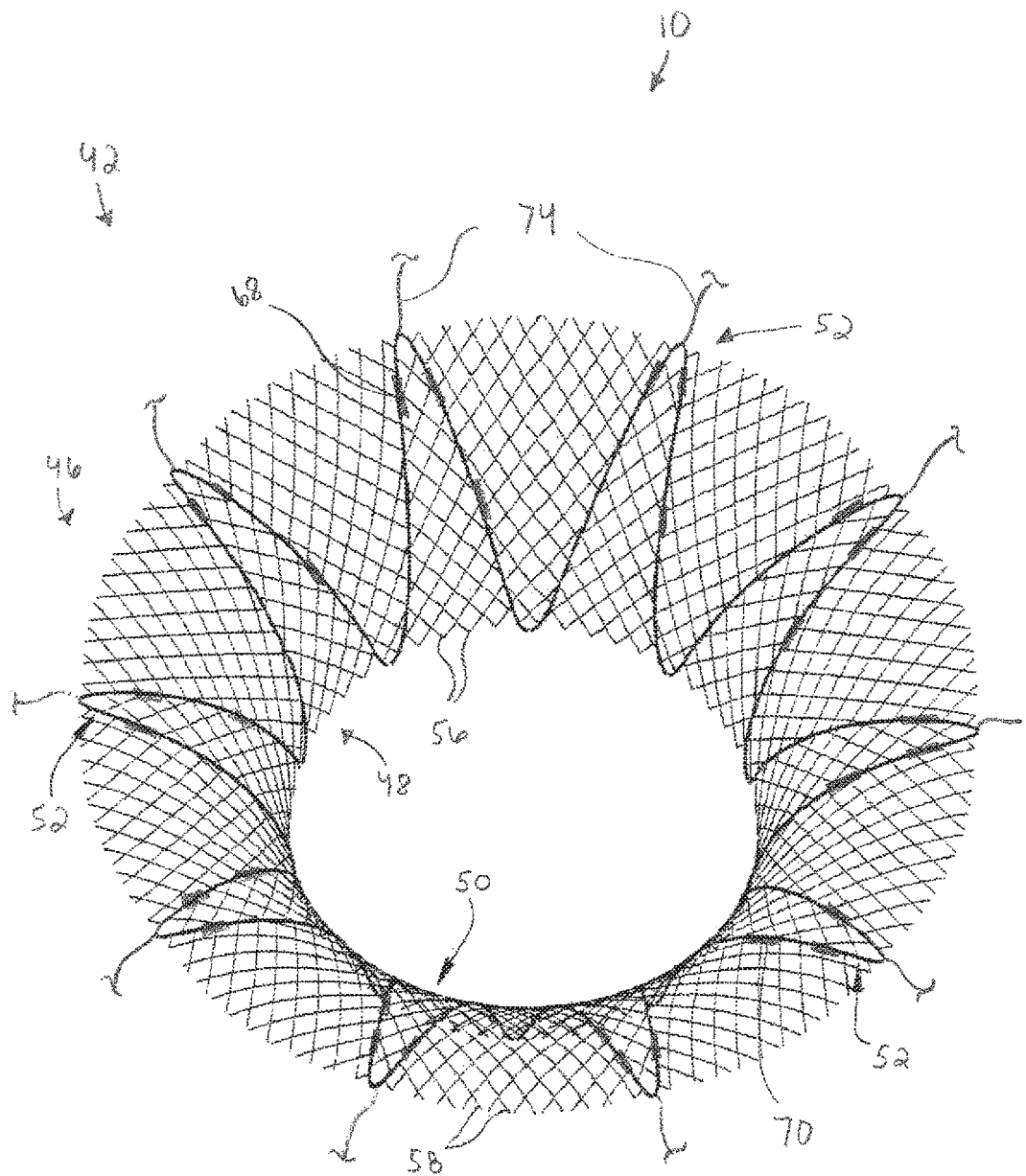
FIG. 3 is a perspective view showing an alternate configuration of the apparatus in FIGS. 1A-C.

The expandable support member 42 can comprise a continuous series of W-shaped segments 54 collectively forming a mesh-like configuration. It is contemplated, however, that other geometries may be used. Lower tips 56, as viewed in FIG. 1A, of the W-shaped segments 54 can form the distal end portion 48 of the expandable support member 42, and upper tips 58 of the W-shaped segments can form the proximal end portion 46 of the expandable support member. As shown in FIG. 1A, for example, both the wing members 52 and the main body portion 50 of the expandable support member 42 may have a mesh-like configuration. Alternatively, the entire main body portion 50, including the wing members 52, may have a mesh-like configuration as illustrated in FIG. 3.

Referring to FIG. 1B, the main body portion 50 of the expandable support member 42 is defined by a length L' that extends between the proximal and distal end portions 46 and 48. The main body portion 50 has a generally cylindrical shape and is adapted to conform to the three-dimensional shape of a pulmonary vein 28. The main body portion 50 may also have a conical shape, depending on the geometry of the pulmonary vein 28. The size of the main body portion 50 may be varied as needed. For example, the circumference and/or diameter of the main body portion 50 may be varied so that the expandable support member 42 more readily conforms to the shape of the pulmonary vein 28. Additionally or optionally, the length L' of the main body portion 50 may also be increased or decreased as needed (e.g., to facilitate implantation in a pulmonary vein 28). In one example, the length L' of the main body portion 50 can be equal to the length L of one or more of the wing members 52. Alternatively, the length L' of the main body portion 50 can be less than or greater than the length L of one or more of the wing members 52.

Figure 4:
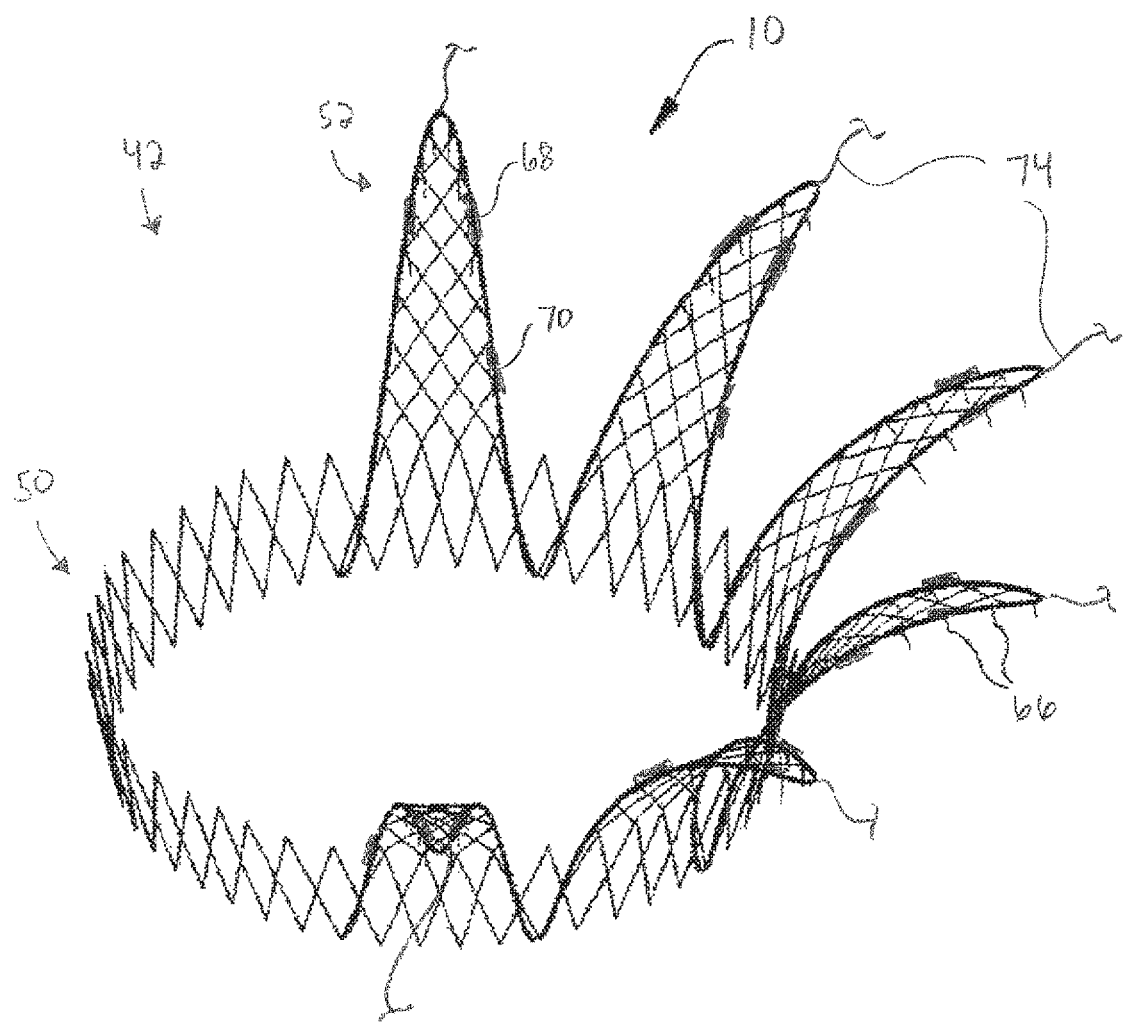
FIG. 4 is a perspective view showing another alternative configuration of the apparatus in FIGS. 1A-C.

In another aspect noted above, the proximal end portion 46 of the expandable support member 42 can include one or more wing members 52 that resemble arches and which extend integrally from the main body portion 50 generally in the proximal direction. In one example, one or more of the wing members 52 can have a length L of about 5 mm to about 12 mm. Each of the wing members 52 can include a free end 60 (e.g., not directly attached to any other structure or component), which is defined by oppositely disposed first and second major surfaces 62 and 64. The first major surface 62 of each wing member 52 is configured to face the interior of the atrial chamber when the apparatus 10 is temporarily implanted. The second major surface 64 (e.g., the entire portion of the second major surface) of each wing member 52 is configured to conform to the surface topography of the atrial tissue comprising the antrum 40 of the pulmonary vein 28 (when the apparatus 10 is temporarily implanted), which advantageously promotes effective lesion formation. In some instances, the apparatus 10 can include eleven wing members 52 spaced about the circumference of the proximal end portion 46. In other instances, more or less than eleven wing members 52 may be used (FIG. 4). It will be appreciated that both the proximal and distal end portions 46 and 48 of the expandable support member 42 may include one or more wing members 52.

Figure 5:
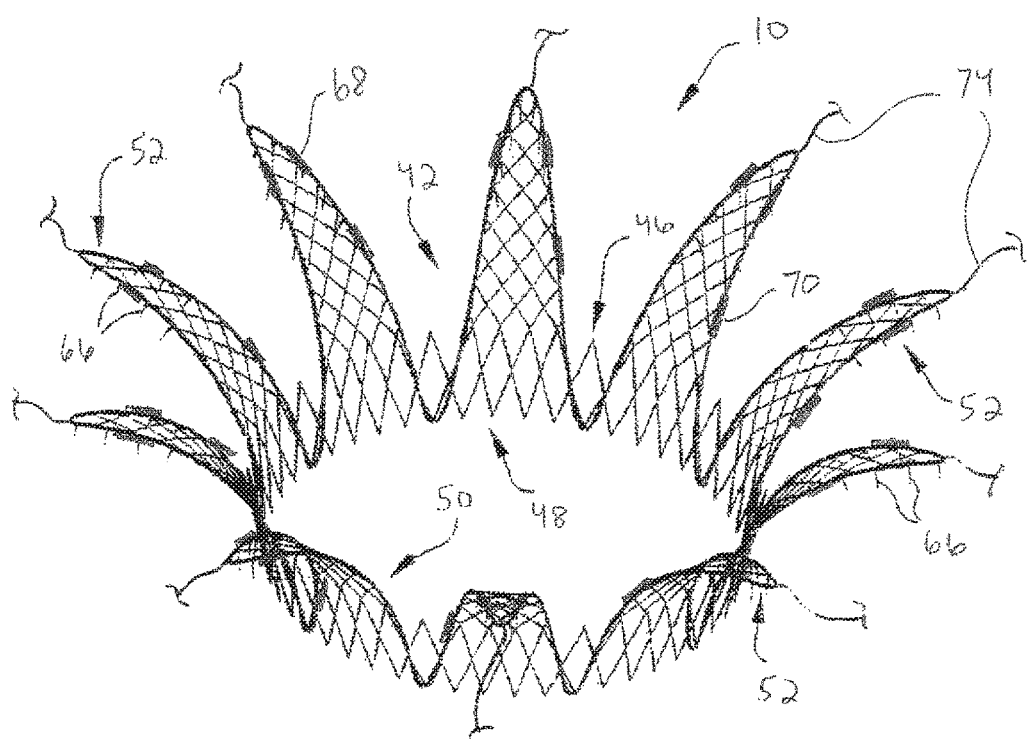
FIG. 5 is a perspective view showing another alternative configuration of the apparatus in FIGS. 1A-C.

The wing members 52 are shaped for conforming to the shape of an antrum 40 of an atrial chamber surrounding a pulmonary vein 28. The wing members 52 are resiliently bendable and are movable from a radially collapsed configuration (not shown) to a radially expanded condition (FIG. 1A) for delivery and placement of the expandable support member 42. As shown in FIG. 1C, each of the wing members 52 can be spaced apart from one another by a distance D, which may be the same (e.g., equidistant wing members) or different. In some instances, equidistant wing members 52 permit creation of a simultaneous and continuous lesion during operation of the apparatus 10. In some instances, one or more of the wing member 52 can include at least one temporary attachment mechanism 66 (FIGS. 4-5), such as a hook or barb for embedding into cardiac tissue to help temporarily secure the expandable support member 42 in a pulmonary vein 28.

Figure 6A:
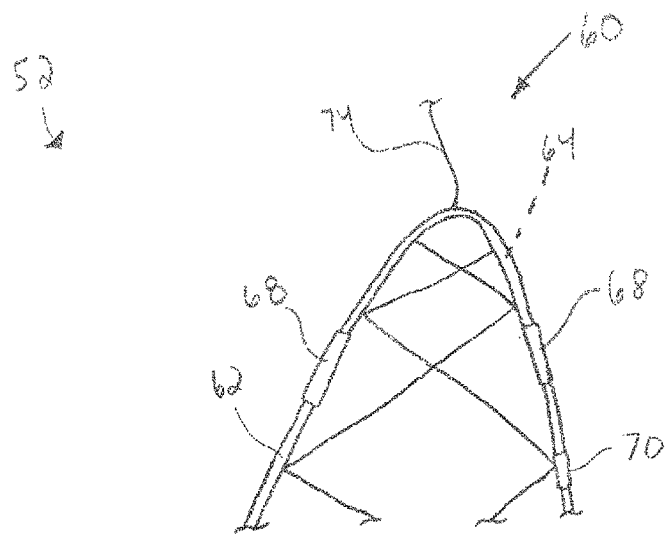
FIG. 6A is a magnified view of a wing member comprising the apparatus in FIGS. 1A-C.
Figure 6B:
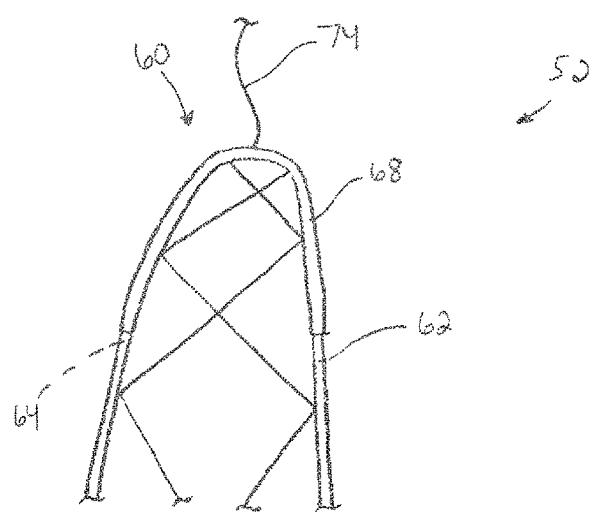
FIG. 6B is a magnified view showing an alternative configuration of the wing member in FIG. 6A.

In another aspect, one or more of the wing members 52 can include at least one ablation element 68 for delivering energy (e.g., electrical energy) to atrial tissue. As shown in FIGS. 6A-B, at least one ablation element 68 is located at or about the free end 60 of each wing member 52. Although two ablation elements 68 are illustrated in FIG. 6A, it will be appreciated that any number of ablation elements can be located at or about the free end 60 of each wing member 52. In some instances, each wing member 52 can include the same number of ablation elements 68. In other instances, each wing member 52 can include a different number of ablation elements 68 as compared to other wing members. The ablation elements 68 can be oppositely disposed and essentially parallel to each other, as shown in FIG. 6A or, alternatively, the ablation elements can be radially or axially offset from one another. For example, the ablation elements 68 may be axially aligned with one another (e.g., on the same wire filament comprising a given wing member 52). The ablation elements 68 can have the same or different shapes. As shown in FIG. 6A, for example, each of the ablation elements 68 can have a cylindrical shape. An ablation element 68 can alternatively have a horseshoe-shaped configuration as shown in FIG. 6B. In one example, an ablation element 68 can comprise an electrode made of any one or combination of electrically-conductive materials, such as activated iridium, rhodium, titanium, platinum, and the like. As discussed in more detail below, electrical energy can be delivered to all the ablation elements 68 at the same time (e.g., simultaneous) or, alternatively, to different ablation elements at different times.

In another aspect, one or more of the wing members 52 can include at least one mapping electrode 70 (FIG. 6A) configured for electrophysiological mapping. As discussed in more detail below, mapping electrodes 70 can facilitate positioning of the apparatus 10 during implantation and, in particular, mapping electrodes can facilitate positioning of the wing members 52 to optimize ablation of antrum atrial tissue. As shown in FIG. 6A, each wing member 52 can include a single mapping electrode 70. Mapping electrodes 70 can have any desired shape and be made of one or more electrically-conductive materials, such as those listed above. It will be appreciated that a mapping electrode 70 and an ablation element 68 may comprise the same element or structure.

In another aspect, the apparatus 10 can include a temperature sensor (not shown) or sensors, such as one or more thermocouples for temperature sensing during an ablation procedure. In one example, temperature monitoring or control can be incorporated into the apparatus 10 by, for example, placing temperature sensors on one or more wing members 52 so that the temperature sensors are located on the second major surface 64 of each wing member. In some instances, "temperature monitoring" can refer to temperature reporting and display for physician interaction. In other instances, "temperature control" can refer to the capability of adding an algorithm in a feedback loop to titrate power based on temperature readings from the temperature sensors. Temperature sensors can provide a means of temperature control by, for example, dividing the apparatus 10 into electrically independent sectors, each with a temperature sensor or, alternatively, each with a mechanism (not shown) to measure impedance to facilitate power titration. In another example, the apparatus 10 may be divided into electrically independent sectors so as to provide zone control. The provision of such sectors can be used to provide power control to various sections (e.g., the wing members) of the apparatus 10.

In another aspect, the apparatus 10 can include one or more pressure sensors (not shown) for detecting pressure between the apparatus (e.g., the wing members 52) a portion of a pulmonary vein 28 and/or the antrum 40.

In another aspect, the apparatus 10 can additionally or optionally include an integrated or separate cooling mechanism (not shown), such as means for delivering a cooling solution (e.g., saline) to the apparatus before, during, or after use. In one example, one or more fluid conduits (not shown) can be connected at a distal end thereof to one or more of the wing members 52. A cooling solution can then be delivered through the fluid conduit(s) during operation of the apparatus 10 so that the fluid is flowed over the wing member(s) 52 and thereby minimizes any increases in local temperature associated with an ablation procedure.

In another aspect, at least a portion of the expandable support member 42 can be treated with one or more therapeutic agents for elution into a blood vessel (e.g., pulmonary vein 28), an atrial chamber, and/or an atrial wall (e.g., antrum wall). A therapeutic agent may be capable of preventing a variety of pathological conditions including, but not limited to, arrhythmias, thrombosis, stenosis, apoptosis, and inflammation. In some instances, a therapeutic agent may include at least one of the following: an anti-arrhythmic agent; anticoagulant; an antioxidant; a fibrinolytic; a steroid; an anti-apoptotic agent; an anti-overgrowth agent (i.e., capable of preventing epithelial cell overgrowth); and/or an anti-inflammatory agent. Optionally or additionally, a therapeutic agent may be capable of treating or preventing other disease or disease processes, such as microbial infections and heart failure. In these instances, a therapeutic agent may include an anti-microbial agent, an inotropic agent, a chronotropic agent, and/or a biological agent such as a cell or protein. More specific types of therapeutic agents, as well as biological agents that may be used as part of the present disclosure are disclosed in U.S. patent application Ser. No. 11/789,827.

In another aspect, the retrieval mechanism 72 of the apparatus 10 is configured to remove the expandable support member 42 (e.g., from a pulmonary vein 28) and energize one or more of the ablation elements 68. One example of the retrieval mechanism 72 is shown in FIG. 1A. Other examples of retrieval mechanism 72 are discussed below. As shown in FIG. 1A, the retrieval mechanism 72 can include one or more electrically-conductive wires 74, each of which is separately connected to a respective one of the wing members 52. In one example, one or more of the electrically-conductive wires 74 can be directly connected to a respective ablation element 68. Each of the electrically-conductive wires 74 includes a proximal end (not shown) and a distal end 76. As shown in FIG. 1A, the distal end 76 of each electrically-conductive wire 74 can be securely and directly connected to a free end 60 of each wing member 52. In some instances, the proximal end of each of the electrically-conductive wires 74 can converge into a single wire, which may be manipulated to control deployment and withdrawal of the apparatus 10. The electrically-conductive wires 74 comprising the retrieval mechanism 72 can be made of any one or combination of flexible materials, such as those discussed above. Advantageously, the retrieval mechanism 72 enables an operator to easily and quickly manipulate the apparatus 10 during a procedure, thereby reducing the risk of inadequate positioning and impaired patient safety.

In another aspect, the apparatus 10 can include an associated electrical mechanism (not shown) for delivering electrical energy to the ablation elements 68. The electrical mechanism can include, for example, an antenna and a power source coupled to the expandable support member 42, along with an externally located device capable of generating an electrical energy signal. Delivery of electrical energy may be achieved by delivering RF energy, microwave energy, laser, ultrasonic energy, freezing (i.e., cryoablation), or any other type of appropriate energy to one or more of the ablation elements 68. To select for different capacitive and resistive effects, it will be appreciated that the expandable support member 42 may be formed from different biocompatible metals, such as platinum iridum alloys, ND35N, titanium, Nitinol, and stainless steel.

Figure 7:
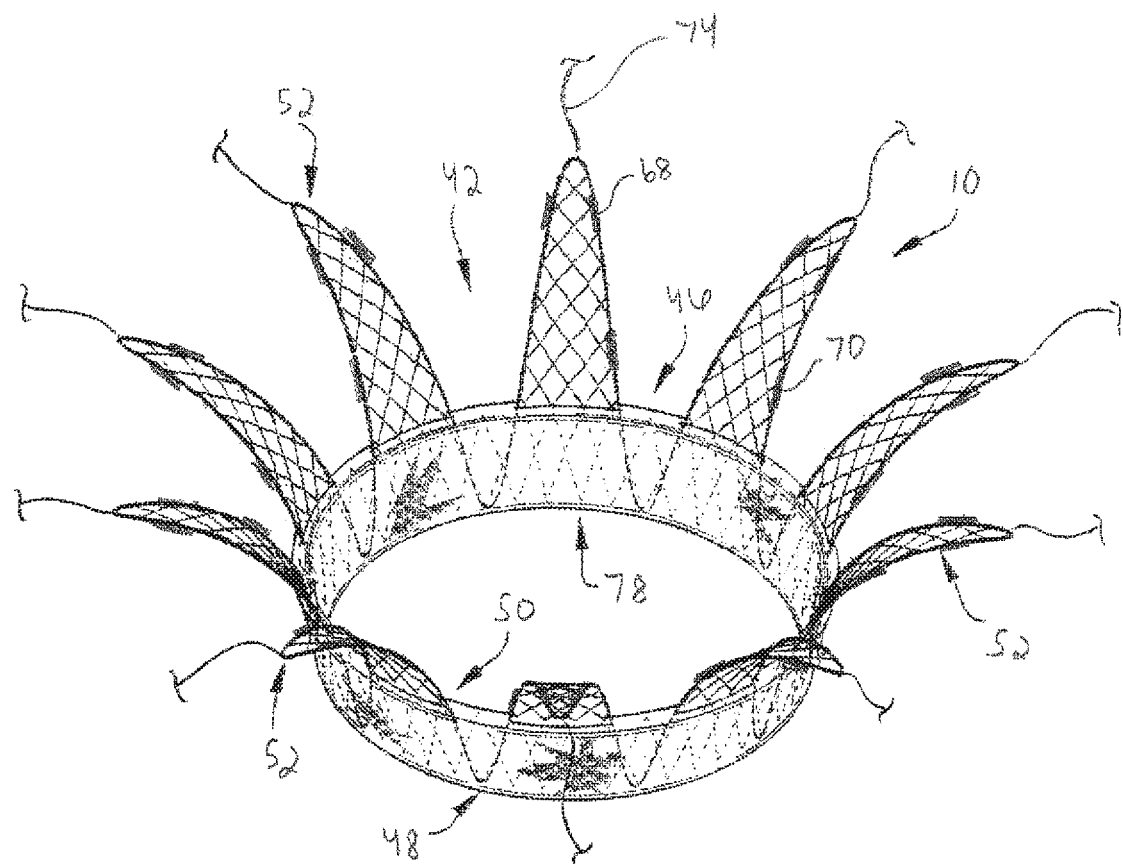
FIG. 7 is a perspective view showing another alternative configuration of the apparatus in FIGS. 1A-C.

In another aspect, the apparatus 10 can include a layer of biocompatible material 78 (FIG. 7) covering at least a portion of the expandable support member 42. As shown in FIG. 7, the main body portion 50 may be covered with the layer of biocompatible material 78. It will be appreciated, however, that the layer of biocompatible material 78 may cover any combination of other portions of the expandable support member 42, such as only the wing members 52 or both the wing members and the main body portion 50. The layer of biocompatible material 78 may be a synthetic material, such as DACRON (Invista, Witchita, Kans.), GORE-TEX (W. L. Gore & Associates, Flagstaff, Ariz.), woven velour, polyurethane, polytetrafluoroethylene (PTFE), expanded PTFE (ePTFE), or heparin-coated fabric. Alternatively, the layer of biocompatible material 78 may be a biological material, such as bovine or equine pericardium, peritoneal tissue, an allograft, a homograft, patient graft, or a cell-seeded tissue. The layer of biocompatible material 78 can cover either the inside surface of the expandable support member 42, the outside surface of the expandable support member, or can be wrapped around both the inside and outside surfaces. The layer of biocompatible material 78 may be attached around the entire circumference of the expandable support member 42 or, alternatively, may be attached in pieces or interrupted sections to allow the expandable support member to more easily expand and contract.

Figure 8:
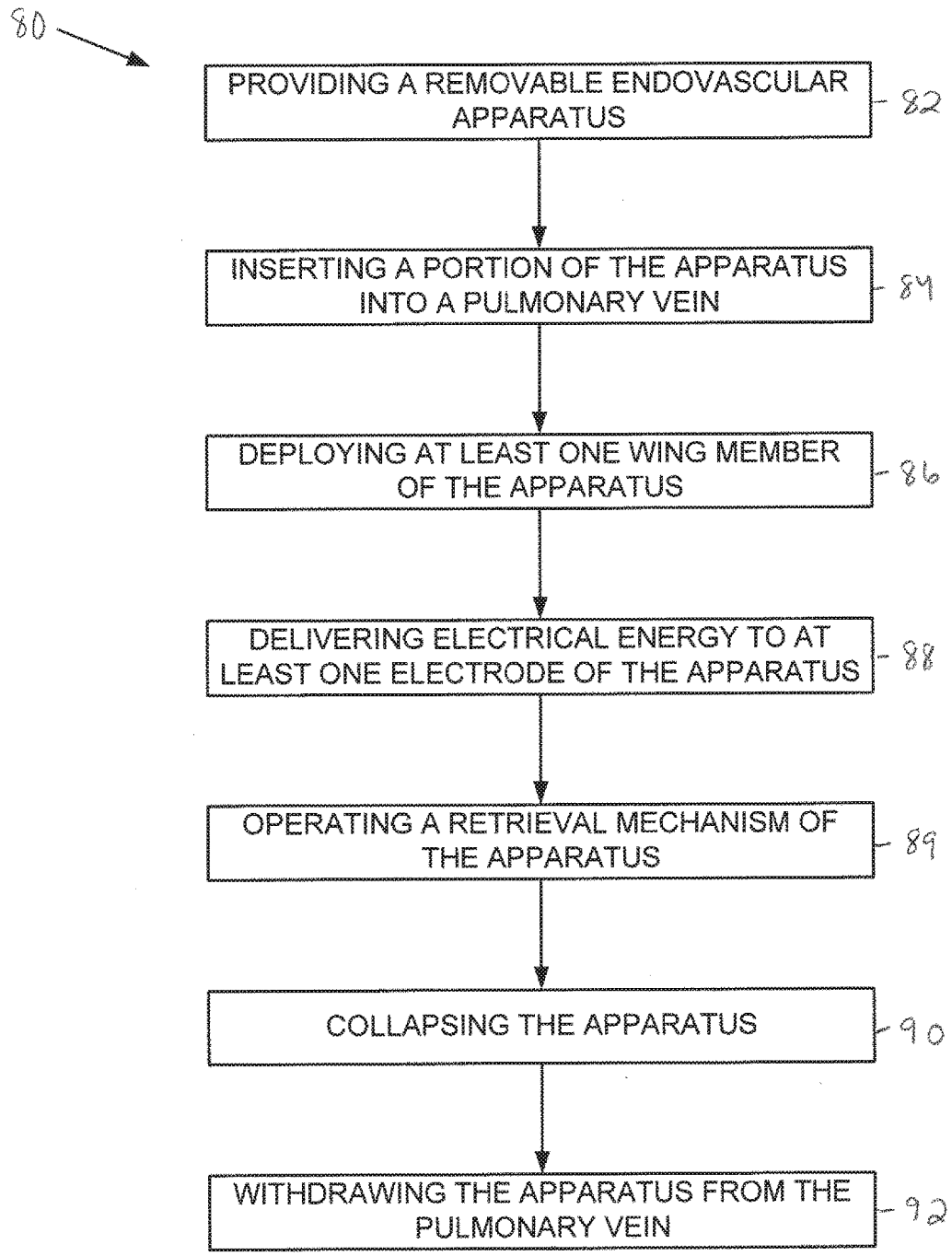
FIG. 8 is a process flow diagram illustrating a method for treating AF in a subject according to another aspect of the present disclosure.

Another aspect of the present disclosure is illustrated in FIG. 8 and includes a method 80 for treating AF in a patient. One step of the method 80 can include providing an apparatus 10 (Step 82). The apparatus 10 can be identically or similarly constructed as the apparatus shown in FIGS. 1A-C, or any other of the configurations described herein. For example, the apparatus 10 can comprise an expandable support member 42 having a main body portion 50, one or more wing members 52 extending from the main body portion, and a retrieval mechanism 72.

Using a percutaneous approach, the patient's left atrium 16 can first be accessed. Once the left atrium 16 has been accessed, the dimensions of the pulmonary vein 28, the ostium 94 of the pulmonary vein, and the antrum 40 surrounding the ostium can be determined. Various devices and methods for determining the dimensions of cardiac and vascular structures are known in the art. After determining the dimensions of the pulmonary vein 28, the ostium 94 of the pulmonary vein, and the antrum 40, an appropriately-sized apparatus 10 can be selected. More particularly, the selected apparatus 10 will be appropriately dimensioned to the size and shape of the pulmonary vein 28, the ostium 94 of the pulmonary vein, and the antrum 40 surrounding the ostium.

Figure 9:
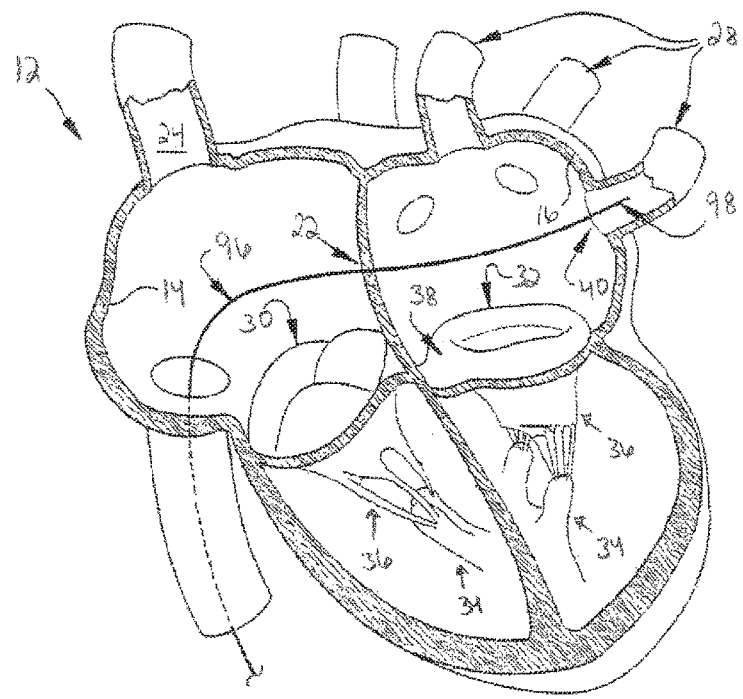
FIG. 9 is a cross-sectional view showing a guidewire extending trans-septally through a human heart.

Next, a guidewire 96 (FIG. 9) can be inserted into a femoral vein (not shown) or jugular vein (not shown) and, under image guidance (e.g., fluoroscopy, ultrasound, magnetic resonance, computed tomography, or combinations thereof), respectively steered through the patient's vasculature into the inferior vena cava 26 or superior vena cava 24. The guidewire 96 can then be passed across the right atrium 14 so that a distal end 98 of the guidewire pierces the interatrial septum 22. Next, the guidewire 96 can be extended across the left atrium 16 into a pulmonary vein 28 so that the distal end 98 of the guidewire is securely positioned in the pulmonary vein.

In one example of a trans-septal approach, a curved needle (not shown in detail), such as a 70 cm curved Brockenbrough needle (USCI, Billerica, Ma.) and a guidewire 80 (e.g., 0.014 inch PTCA guidewire) can be inserted into the stopcock lumen of the needle with an introducer (not shown) to determine the safety of the guidewire and the needle. For the Inoue technique, a dilator (e.g., a Mullins dilator) (not shown) alone can be advanced to the junction of superior vena cava 24 and right atrium 14 over a guidewire (e.g., a 0.032 inch Terumo J guidewire) from the right femoral vein (not shown). After removing the 0.032 inch Terumo J guidewire, the Brockenbrough needle with a 0.014 inch guidewire can be advanced through the Mullins dilator. To avoid perforation of the dilator wall during needle advancement, the 0.014 inch guidewire can be protruded slightly beyond the tip of the needle and then moved in combination (i.e., the needle-wire combination) through the Mullins dilator. The septal puncture can be performed by pulling the 0.014 inch guidewire slightly below the tip of the needle. The angle of the needle for penetration of the septum 22 can be determined by using dimensions from a previous contrast-enhanced CT scan of the left atrium 16. For example, the CT slice showing the longest length of the atrial septum 22 can be used to determine the angle of the needle. The angle of the needle puncture can then be determined simply as the perpendicular angle of the atrial septum 22.

Figure 10:
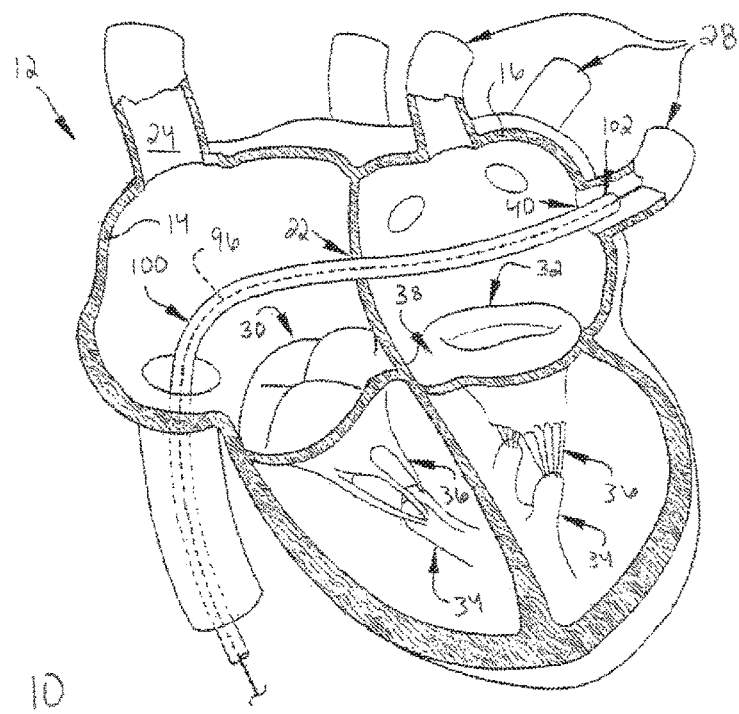
FIG. 10 is a cross-sectional view showing a catheter advanced over the guidewire.
Figure 11:
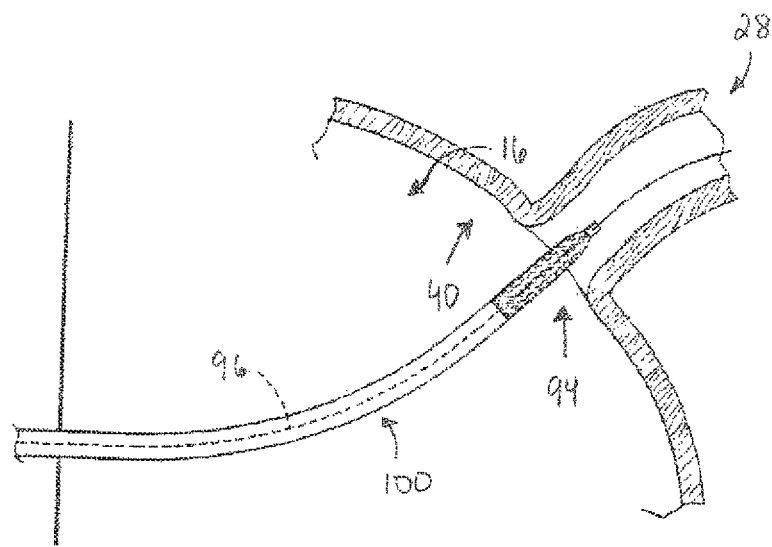
FIG. 11 is a cross-sectional view showing the apparatus in FIGS. 1A-C, in a collapsed configuration, contained in the catheter.
Figure 12:
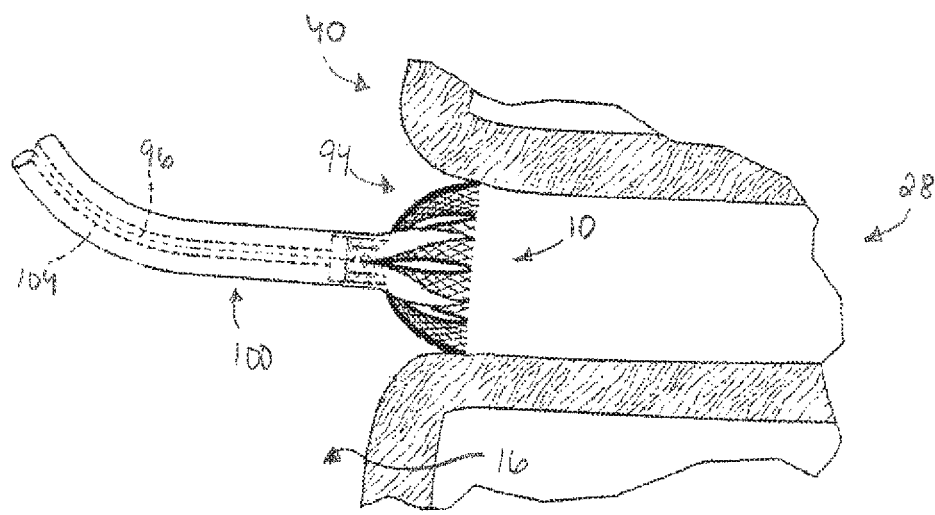
FIG. 12 is a cross-sectional view showing the apparatus in FIG. 11 at an initial stage of delivery in a pulmonary vein.

After the guidewire 96 is passed into the pulmonary vein 28, a catheter 100 or sheath can be passed over the guidewire (FIG. 10). The catheter 100 may be comprised of a flexible, resiliently yieldable material such as silicone, PTFE, ePTFE, plastic polymer, or the like. As shown in FIG. 10, the catheter 100 can be urged along the guidewire 96 until a distal end 102 of the catheter is appropriately positioned in the ostium 94 of the pulmonary vein 28. Next, the apparatus 10, in a collapsed configuration, can be attached to a proximal end (not shown) of the guidewire 96. A pushrod 104 (FIG. 12) or other similar device can then be used to urge the apparatus 10 along the guidewire 96 into the left atrium 16. Once the apparatus 10 is positioned near the distal end 102 of the catheter 100, the catheter may be slowly withdrawn. At Step 84, the main body portion 50 of the expandable support member 42 can be progressively freed from the catheter 100 and self-expand into the pulmonary vein 28 so that the main body portion engages the ostium 94 of the pulmonary vein as the catheter is withdrawn (FIG. 12).

Figure 13:
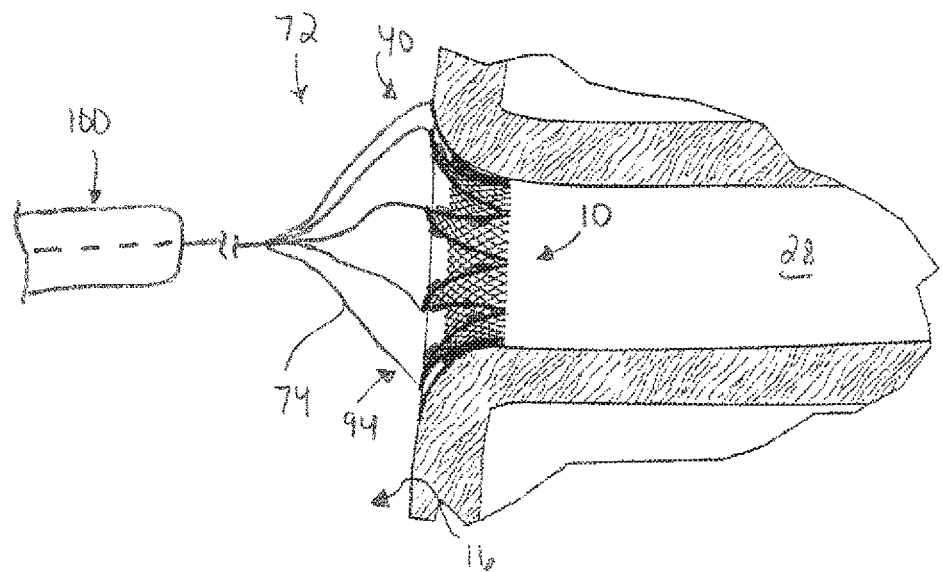
FIG. 13 is a cross-sectional view showing the apparatus in FIG. 12 deployed in the pulmonary vein and in the antrum of the left atrium.

As the expandable support member 42 is further freed from the catheter 100, each of the wing members 52 can expand to their radially expanded configuration (Step 86). As shown in FIG. 13, each of the wing members 52 can expand to engage the antrum 40 surrounding the ostium 94 of the pulmonary vein 28. For example, each of the wing members 52 can be deployed so that the second major surface 64 extends substantially radial to the main body portion 50 and firmly engages the atrial tissue comprising the antrum 40 of the pulmonary vein 28. Once the expandable support member 42 has obtained its expanded configuration, the expandable support member is securely positioned in the ostium 94 of the pulmonary vein 28. The position of the apparatus 10 may then be varied, if needed, by manipulating (e.g., withdrawing) the electrically-conductive wires 74 of the retrieval mechanism 72 and thereby adjusting the position of the wing members 52 and/or the main body portion 50. For example, the main body portion 50 may be moved either more proximate to, or less proximate from, the ostium 94.

Upon positioning the apparatus 10 as desired, energy (e.g., electrical energy) can be delivered to one or more of the ablation elements 68 (Step 88). To do so, a surface electrode (not shown) can be mounted on the patient's body (e.g., on the patient's back) to permit the use of the ablation elements 68 in a monopolar mode. Alternatively, a return electrode (not shown) may be provided on the apparatus 10, e.g., proximal to the wing members 52. Prior to delivery of electrical energy, an operator can analyze electrical signals detected by the mapping electrode(s) 70 to determine if the one or more of the wing members 52 has been placed over an arrhythmogenic focus. If so, the operator may energize any of the ablation elements 68, as appropriate, to ablate the focus. In one example, bipolar RF energy may be applied between pairs of the ablation elements 68 or, alternatively, monopolar energy may be applied to any one of the ablation elements (e.g., grounded to a surface electrode or a return electrode located proximally on the apparatus 10).

For each arrhythmogenic focus, an appropriate ablation element 68 (or ablation elements) can be energized to direct ablative RF power to the antrum atrial tissue and away from the ostium 94 and the pulmonary vein 28 itself. Advantageously, the pulmonary vein 28 does not receive RF energy, thereby avoiding damage the pulmonary vein. In one example, electrical energy can be delivered to each of the ablation elements 68, at the same time, to simultaneously create a continuous lesion. In such instances, operation of the device 10 achieves a complete conduction block because there is no need to lift or drag the ablation elements 68 along the arrhythmogenic focus and thereby risk creating gaps or spaces between lesions, which permit some conduction therethrough. In some instances, treatment of the antrum atrial tissue may include the additional steps of ablating the antrum atrial tissue with the ablation element(s) 68 in a first orientation, then operating the retrieval mechanism 72 to rotate the apparatus 10 while maintaining (or re-establishing) contact between the ablation element(s) and the antrum atrial tissue to establish contact in a second orientation, and then ablating the antrum atrial tissue with the ablating element(s) in the second orientation. These steps may be repeated as necessary to create a substantially circumferential lesion in the antrum atrial tissue. If needed, the apparatus 10 can be repositioned in a second pulmonary vein 28 and the method 80 repeated to ablate additional atrial tissue. Advantageously, positioning of the wing members 52 (and thus the ablation elements 68) about the ostium 94 of a pulmonary vein 28 avoids undesirable ablation of the pulmonary vein itself, which can produce stenosis. The wing members 52 also stabilize the apparatus 10 during the procedure, which further helps to avoid ablation within a pulmonary vein 28. Additionally, the configuration of the wing members 28 ensures full contact of the ablation elements 68 with the antrum atrial tissue, thereby producing more effective lesions and decreasing the amount of energy required to create the lesions.

It will be appreciated that a control level of energy can be delivered to the ablation element(s) 68 and then tested for lesion formation with a test stimulus by, for example, an electrode on a separate device (e.g., a guidewire). Therefore, in some instances, the method 80 may involve ablation at a first energy level in time, checking for an effective conductive block provided by the resulting lesion, and then subsequent ablations and testing until a complete conductive block is formed. In other instances, the apparatus 10 may include feedback control if, for example, thermocouples are included as part of the apparatus. Monitoring temperature at a given location can thus provide indicia for the progression of the lesion.

Figure 14:
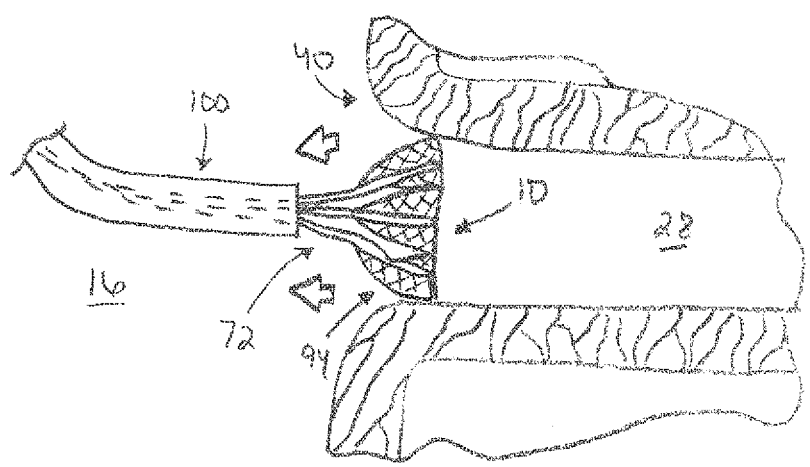
FIG. 14 is a cross-sectional view showing the apparatus in FIG. 13 being withdrawn from the pulmonary vein using a retrieval mechanism.
Figure 15A:
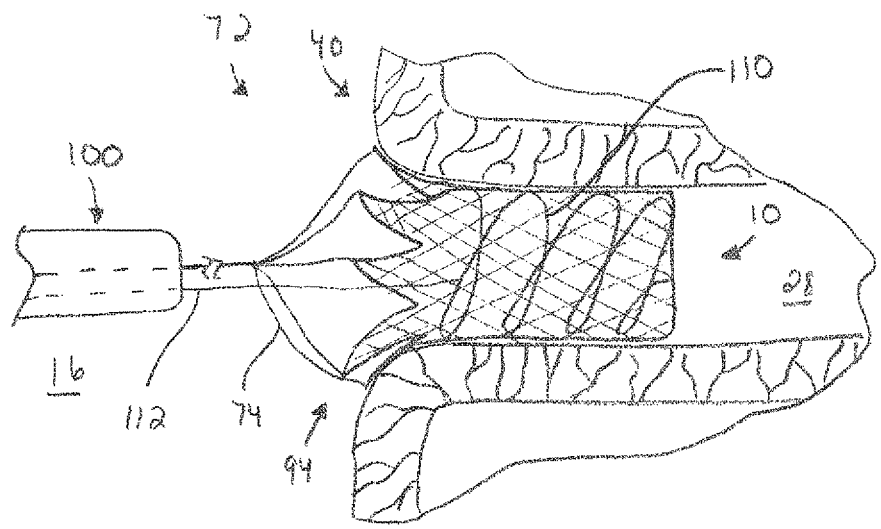
FIGS. 15A-B are cross-sectional views showing the apparatus in FIG. 13 being withdrawn from the pulmonary vein and in the antrum of the left atrium using an alternative configuration of the retrieval mechanism in FIG. 14.
Figure 15B:
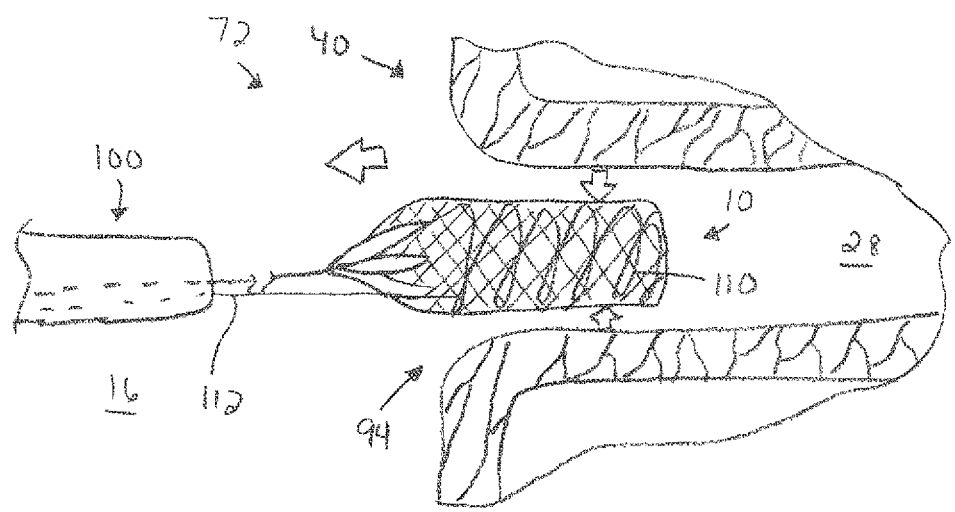

Following ablation of the antrum atrial tissue, the apparatus 10 can be removed from the pulmonary vein 28 using the retrieval mechanism 72 (Step 89). As shown in FIG. 14, for example, the retrieval mechanism 72 can be manipulated so that the electrically-conductive wires 74 are withdrawn into the delivery catheter 100, which causes each of the wing members 52 to transition into the radially collapsed configuration. Alternatively, the apparatus 10 can be removed from the pulmonary vein 28 using the retrieval mechanism 72 shown in FIGS. 15A-B. In some instances, the retrieval mechanism 72 can further include at least one internal coiled wire 110. The coiled wire 110 can be securely affixed to one or more interior surfaces of the expandable support member 42. The coiled wire 110 can be made of a metal or a metal alloy, such as stainless steel or a shape memory material. As shown in FIG. 15A, the coiled wire 110 can expand in concert with the expandable support member 42 during deployment of the apparatus 10. To withdraw the apparatus 10, a control wire 112 can be manipulated (e.g., pulled), which causes the expandable support member 42 to collapse radially (indicated by arrows in FIG. 15B). The apparatus 10 can then be safely withdrawn from the pulmonary vein 28. Once the apparatus 10 has been completely collapsed into the delivery catheter 100 (Steps 90-92), the delivery catheter can be withdrawn from the patient and the procedure completed. For example, the apparatus 10 can be entirely removed from the patient or, alternatively, an ablation procedure can be performed on another pulmonary vein according to the method 80.

Figure 16A:
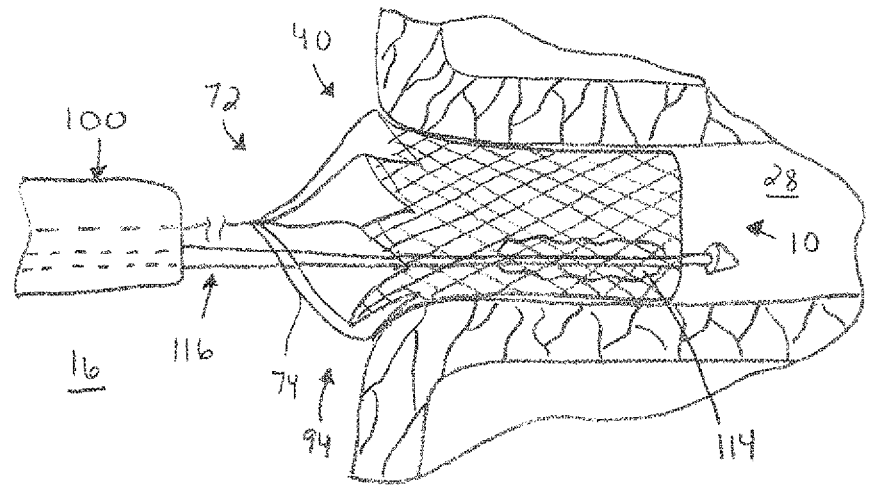
FIGS. 16A-B are cross-sectional views showing the apparatus in FIG. 13 being withdrawn from the pulmonary vein and in the antrum of the left atrium using another alternative configuration of the retrieval mechanism in FIG. 14.
Figure 16B:
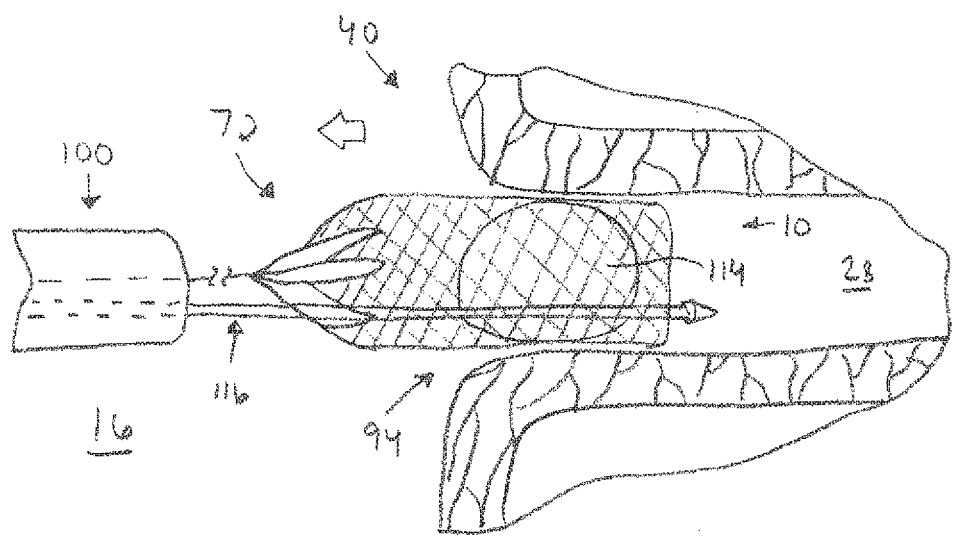

In another example, the apparatus 10 can be removed from the pulmonary vein 28 using the retrieval mechanism 72 shown in FIGS. 16A-B (Step 89). In some instances, the retrieval mechanism 72 can further include an inflation member 114 (e.g., a balloon) that is operably connected to a shaft 116. The shaft 116 can include a lumen (not shown) for delivering an inflation medium to the inflation member 114. As shown in FIG. 16A, the shaft 116 is positioned within the expandable support member 42 following an ablation procedure such that the inflation member 114, in a deflated configuration, is positioned within the lumen of the expandable support member. It will be appreciated that the shaft 116 can be inserted through the apparatus 10 before, during, or after the procedure. To withdraw the apparatus 10, an inflation medium is delivered to the inflation member 114, which causes the inflation member to snugly contact the inner surface of the expandable support member 42. The shaft 116 can then be withdrawn (indicated by arrow in FIG. 16B), which also causes the apparatus 10 to be removed from the pulmonary vein 28. Once the apparatus 10 has been completely collapsed into the delivery catheter 100 (Steps 90-92), the delivery catheter can be withdrawn from the patient and the procedure completed. For example, the apparatus 10 can be entirely removed from the patient or, alternatively, an ablation procedure can be performed on another pulmonary vein according to the method 80.

Advantageously, the apparatus 10 of the present disclosure is able to ablate antrum atrial tissue easily and quickly where it is difficult and time consuming to form the circumferential lesion using conventional RF catheter ablation techniques. In particular, lesions can be more easily formed in comparison to conventional methods because the wing members 52 of the apparatus 10 naturally expand into flush contact with the antrum atrial tissue, and naturally recoil against the atrial wall surrounding the pulmonary vein ostium 94. Thus, the conventionally difficult procedure of maneuvering an ablation catheter to form a circumferential lesion is avoided.

It will be appreciated that the apparatus 10 may implanted using non-percutaneous techniques. For example, an open-chest procedure may be used to implant the apparatus 10 as either a standalone procedure (e.g., CABG) or as a complement to valve and/or heart transplant surgery. Although not shown, it will also be appreciated that a percutaneous retrograde approach can be used to place the apparatus 10. Briefly, for example, a guidewire can be inserted into a femoral artery or jugular artery, steered through the subject's vasculature into the aortic arch (not shown), into the left ventricle 20, across the mitral valve 32 into the left atrium 16, and into a pulmonary vein 28. A catheter can then be passed over the guidewire and urged along until a distal end of the catheter is positioned at or in the pulmonary vein 28. The apparatus 10 can then be advanced to the pulmonary vein 28 and the catheter slowly withdrawn to secure the apparatus in the pulmonary vein.

From the above description of the present disclosure, those skilled in the art will perceive improvements, changes and modifications. Such improvements, changes, and modifications are within the skill of the art and are intended to be covered by the appended claims.

The following is claimed:

1. A removable apparatus for temporary implantation in a pulmonary vein for ablating atrial tissue surrounding the antrum of the pulmonary vein to treat atrial fibrillation in a subject, said apparatus comprising:

an electrically-insulated expandable support member having oppositely disposed proximal and distal end portions and a main body portion extending between said end portions for positioning in the pulmonary vein, said proximal end portion including a series of annularly disposed wing members that are radially spaced apart from each other and extend from said main body portion, each of said wing members having a free end and being defined by oppositely disposed first and second major surfaces, said distal end portion adapted for insertion into the pulmonary vein to accurately position said proximal end portion at the antrum;

when temporarily implanted, said first major surface for facing the interior of the atrial chamber and said second major surface having a shape configured to conform to the surface topography of the atrial tissue without penetrating the atrial tissue surrounding the pulmonary vein;

at least one of said wing members including at least one ablation element for delivering electrical energy to the atrial tissue, said at least one ablation element being located at said free end of at least one of said wing members; and a retrieval mechanism for removing said expandable support member and, optionally, for energizing said at least one ablation element, said retrieval mechanism including at least one electrically-conductive wire, said at least one wire being separately connected to at least one of said wing members.

2. The apparatus of claim 1, wherein each of said at least one wire of said retrieval mechanism is separately connected to a respective one of said at least one ablation element.

3. The apparatus of claim 2, wherein said at least one wire is directly connected to said at least one ablation element.

4. The apparatus of claim 2, wherein said at least one wire is directly connected to at least one free end of said at least one wing member.

5. The apparatus of claim 2, further comprising a plurality of wires, each of which includes a proximal end that converges into a single wire.

6. The apparatus of claim 1, wherein said retrieval mechanism further includes at least one coiled wire disposed within said expandable support member.

7. The apparatus of claim 6, wherein said at least one coiled wire is securely affixed to one or more interior surfaces of said expandable support member.

8. The apparatus of claim 6, wherein said at least one coiled wire expands and collapses in concert with said expandable support member.

9. The apparatus of claim 1, wherein said retrieval mechanism further includes an inflation member operably connected to a shaft.

10. The apparatus of claim 9, wherein said inflation member is disposed within said expandable support member.

11. The apparatus of claim 9, wherein inflation of said inflation member causes said inflation member to snugly contact an inner surface of said expandable support member.

12. The apparatus of claim 11, wherein said expandable support member is withdrawn from the pulmonary vein upon application of an axial force to said shaft.

13. The apparatus of claim 1, wherein said second major surface has a shape configured to conform to the surface topography of the antrum of the pulmonary vein.

14. The apparatus of claim 1, wherein said expandable support member has a first mesh-like configuration and said at least one wing member independently comprises a second mesh-like configuration.

15. The apparatus of claim 1, wherein one or more of the wing members is arch-shaped.

16. The apparatus of claim 1, wherein said retrieval mechanism further comprises a delivery catheter having an opening at a distal end thereof, said at least one electrically-conductive wire extending from said distal end through said opening of said delivery catheter into connection with at least one of said wing members.

* * * * *